(12) United States Patent
Zadini et al.

(10) Patent No.: US 6,217,558 B1
(45) Date of Patent: Apr. 17, 2001

(54) APPARATUS FOR BLOOD VESSEL TYPE DIFFERENTIATION FOR SYRINGES AND GUIDEWIRES PLACEMENT DEVICES

(76) Inventors: Filiberto P. Zadini, 16814 Rayen St., North Hills, CA (US) 91343; Giorgio C. Zadini, 2237 Hilltop La., Camarillo, CA (US) 93012

( * ) Notice: Subject to any disclaimer, the term of this patent is extended or adjusted under 35 U.S.C. 154(b) by 0 days.

(21) Appl. No.: 09/215,517

(22) Filed: Dec. 17, 1998

(51) Int. Cl.[7] ............................ A61M 5/00; A61M 5/178
(52) U.S. Cl. ............ 604/187; 604/164.01; 604/164.13; 604/264
(58) Field of Search .................... 604/117, 187, 604/164, 167, 169, 222, 264

(56) References Cited

U.S. PATENT DOCUMENTS

| | | | |
|---|---|---|---|
| 5,425,718 | * | 6/1995 | Tay et al. ........................ 604/165 |
| 5,522,399 | * | 6/1996 | Wilk et al. ...................... 128/748 |
| 5,722,955 | * | 3/1998 | Racz ................................. 604/121 |

* cited by examiner

*Primary Examiner*—Richard K. Seidel
*Assistant Examiner*—Michael J Hayes
(74) *Attorney, Agent, or Firm*—Gerald E. Helget; Rider Bennett Egan & Arundel

(57) ABSTRACT

An apparatus for vascular access devices such as syringes and guidewires placement devices capable of differentiating type of blood vessel penetrated by a cannula, including a chamber in flow communication with the cannula, the chamber being adapted to house a vacuum pressure to accelerate backflow of blood from a blood vessel penetrated by the cannula and a slideable, displaceable member within the chamber, such as a piston, displaceable against a calibrated pressure sensitive resilient member such as a spring. The displaceable member is displaced against the pressure sensitive spring rearwardly by the blood pressure indicating to the operator the type of blood vessel penetrated by the cannula by the amount of rearward displacement of the piston in respect to a point reference tab located on the side wall of the chamber.

18 Claims, 10 Drawing Sheets

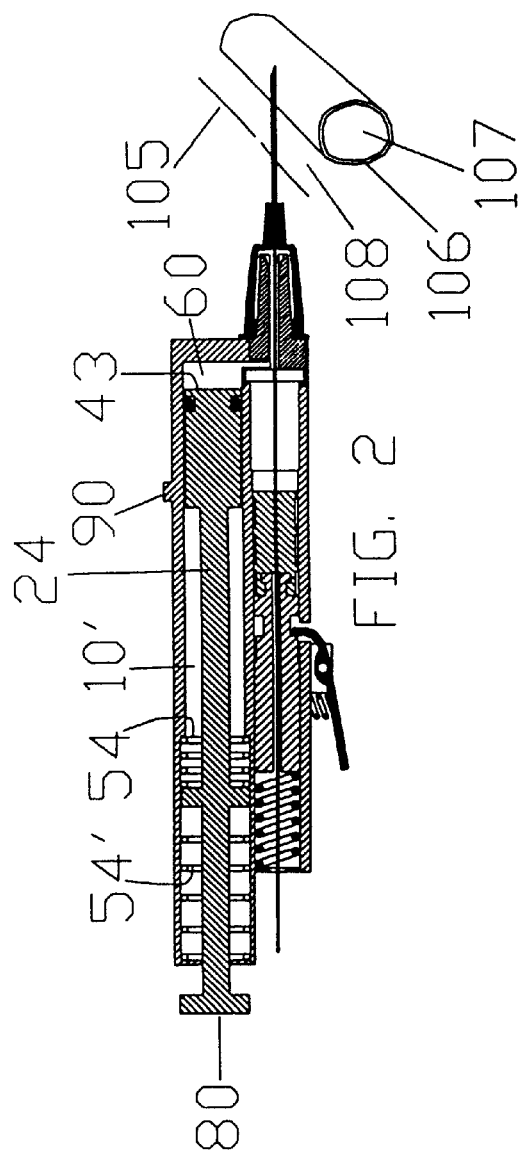
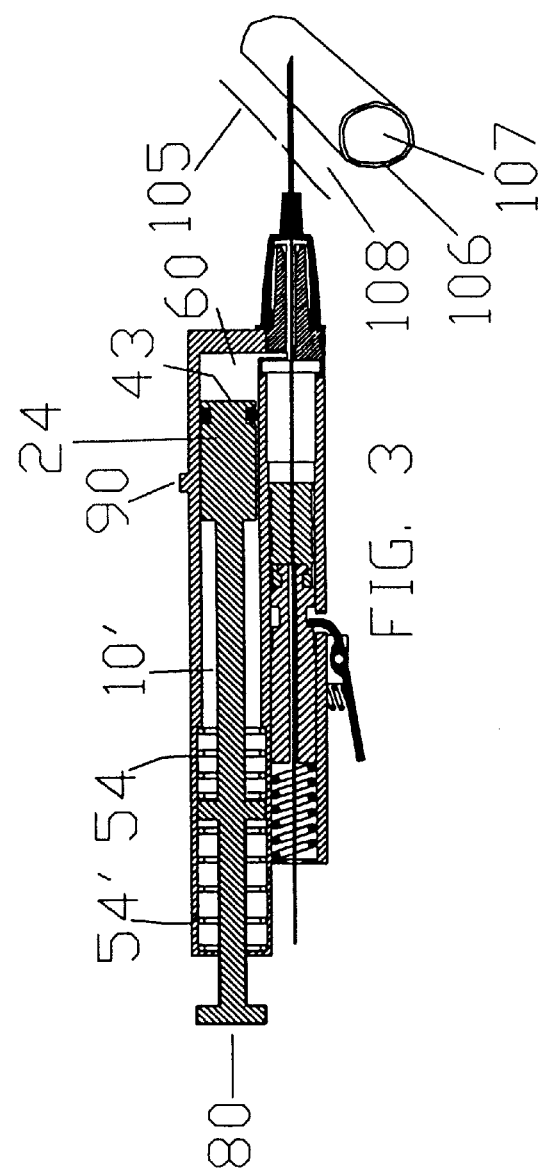

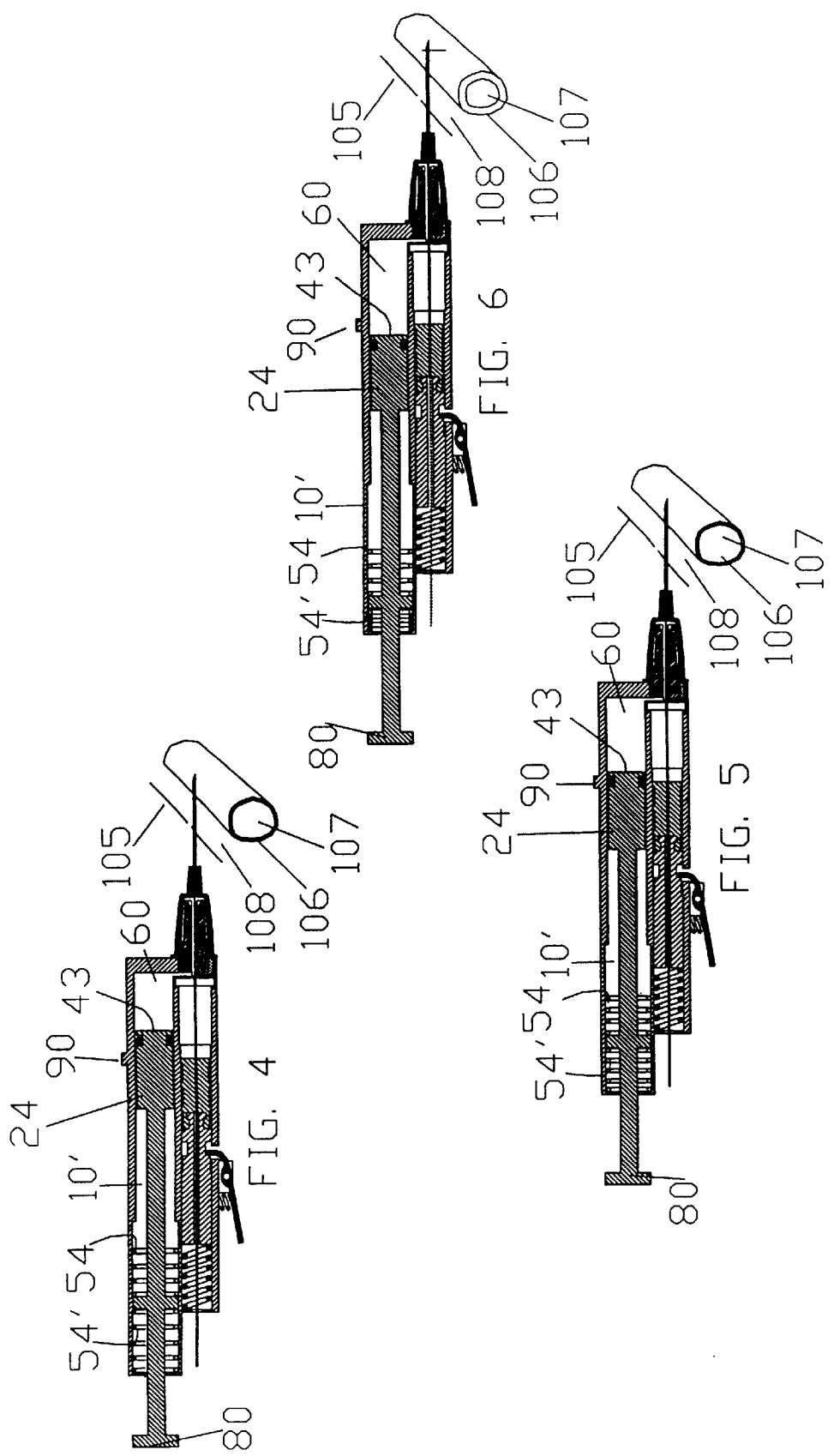

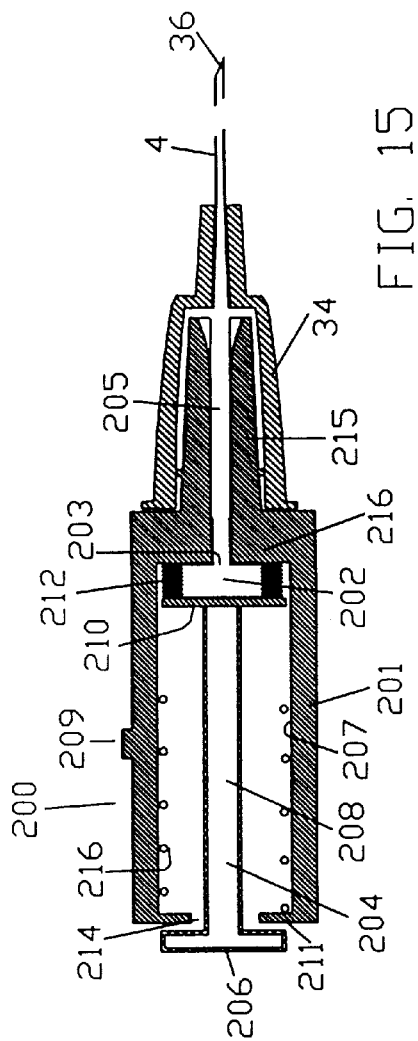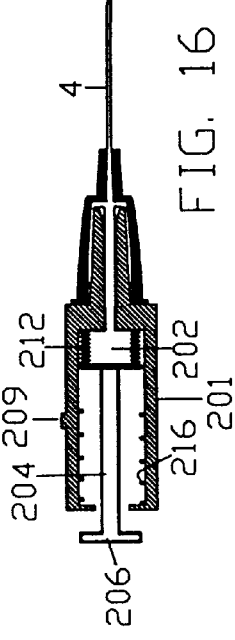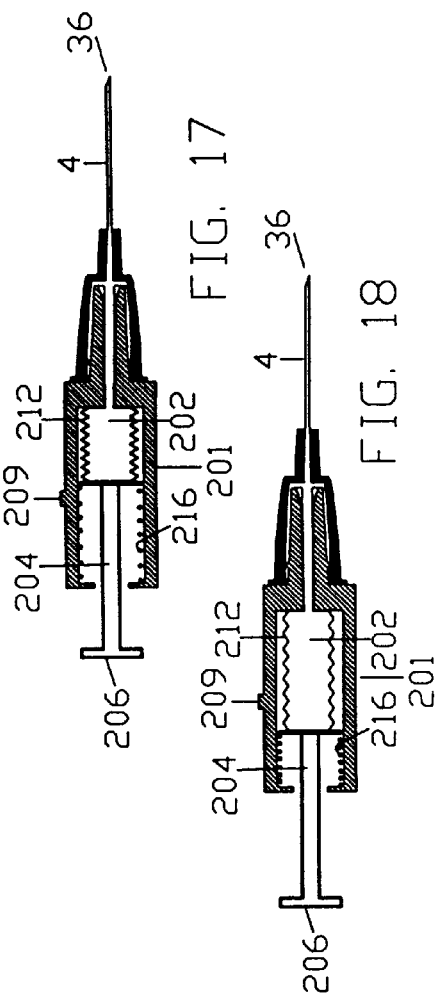
FIG. 15
FIG. 16
FIG. 17
FIG. 18

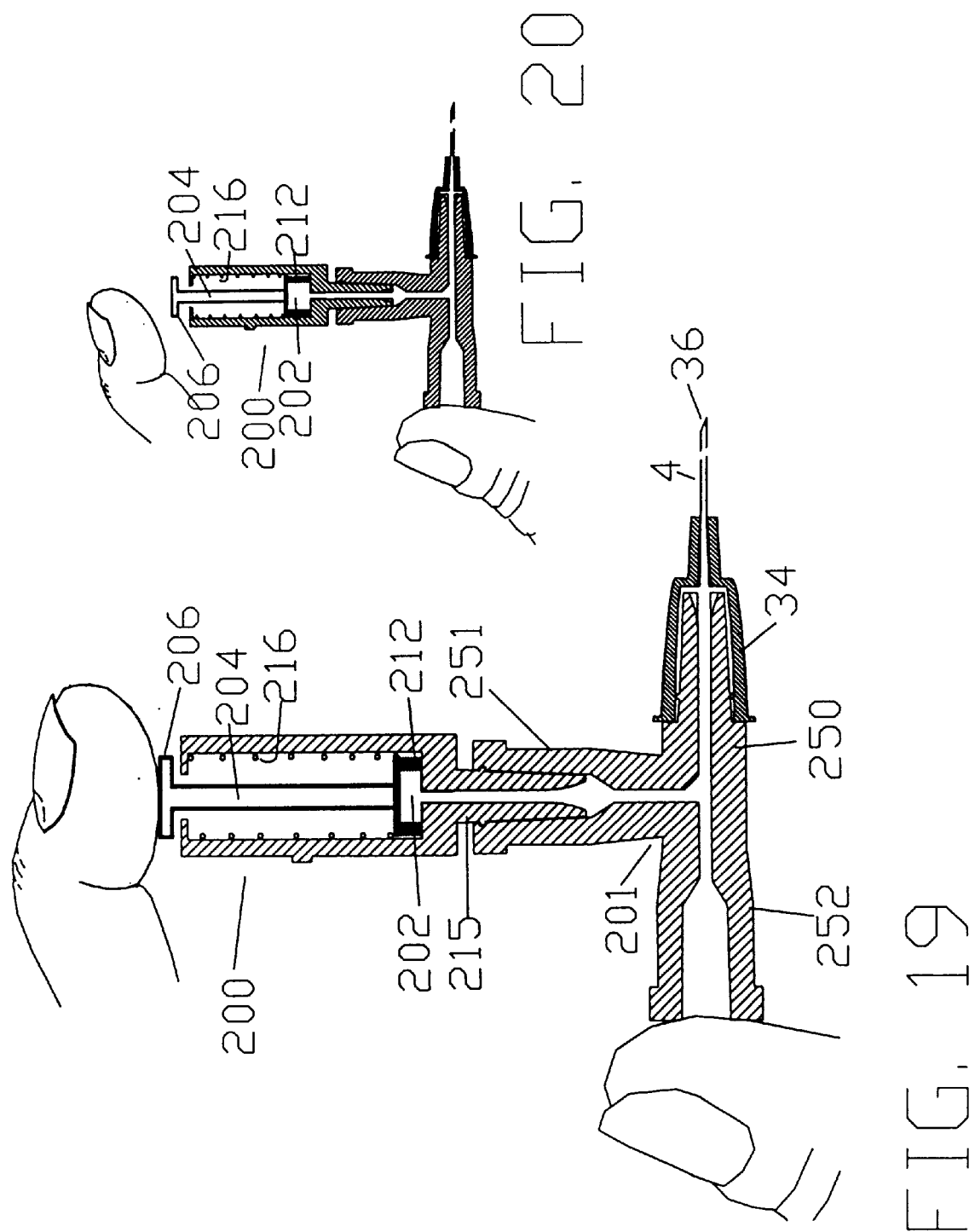

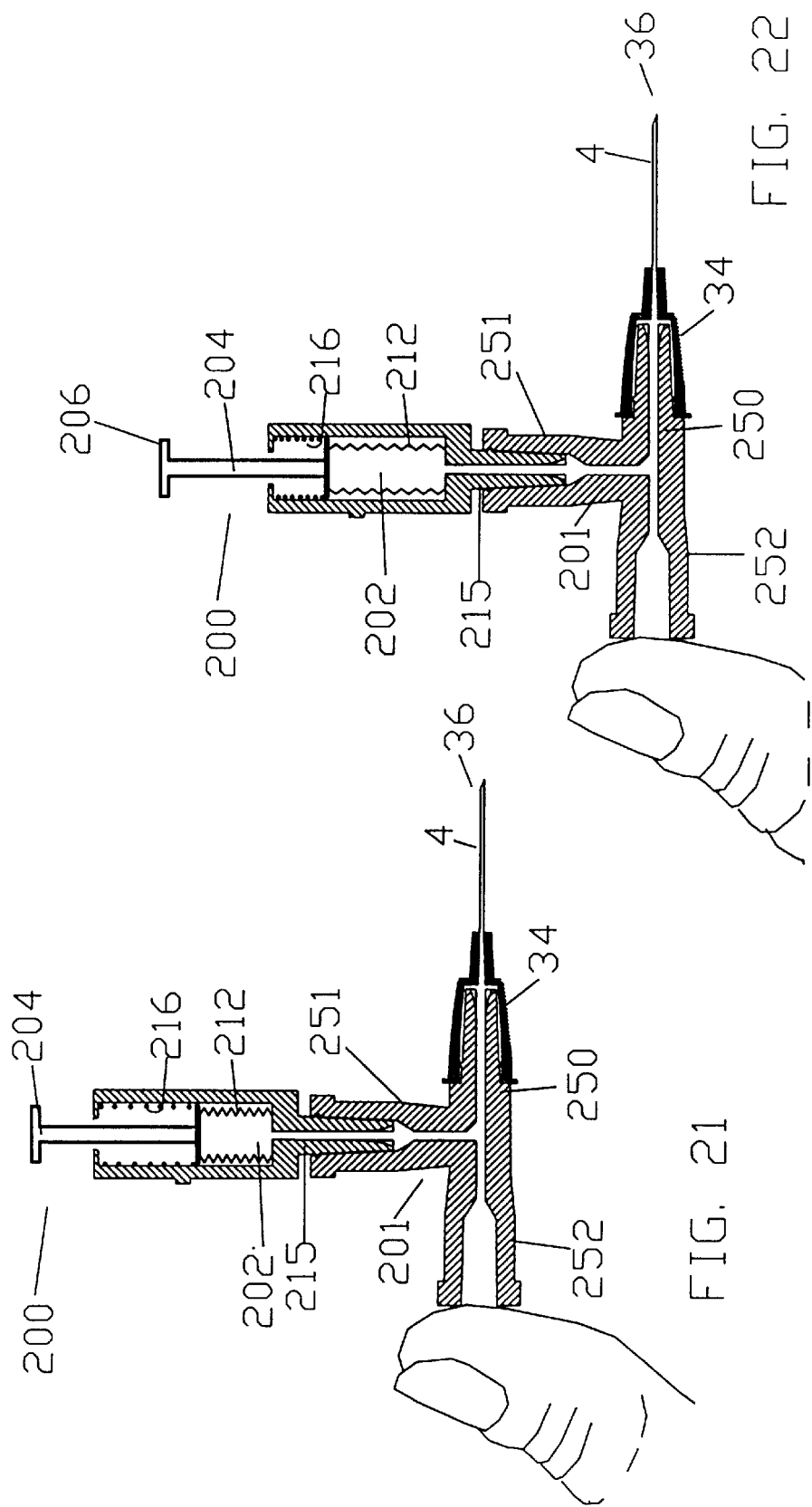

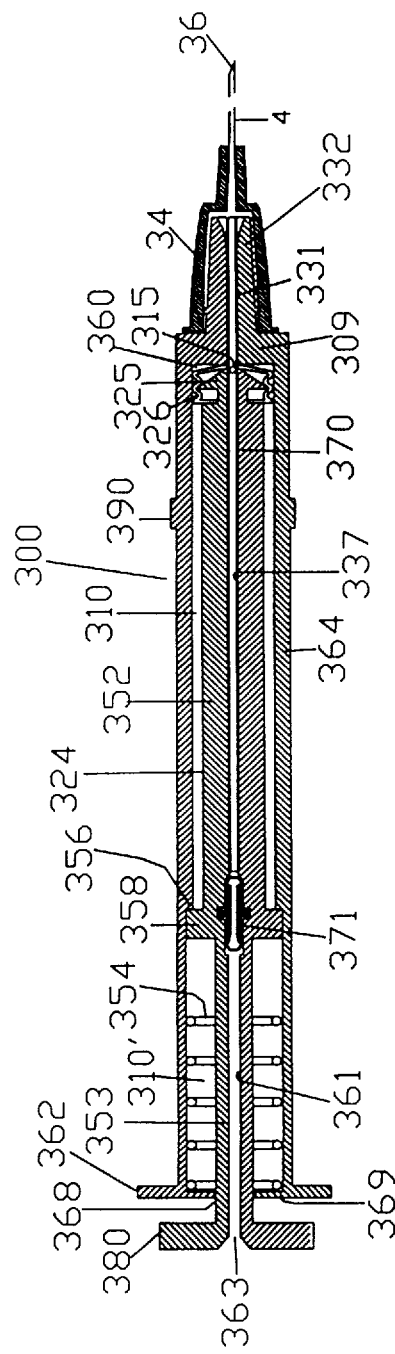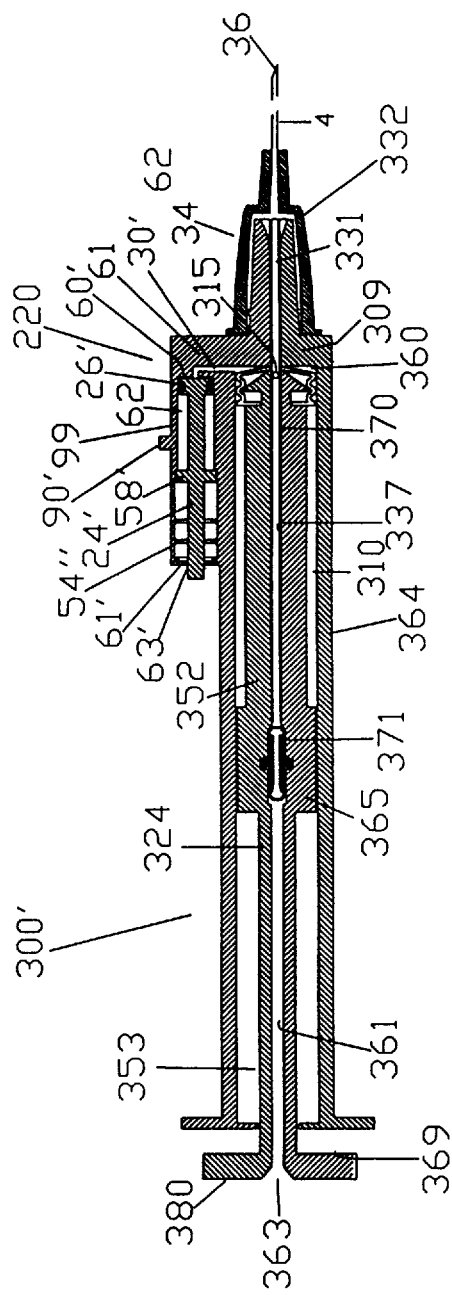

APPARATUS FOR BLOOD VESSEL TYPE DIFFERENTIATION FOR SYRINGES AND GUIDEWIRES PLACEMENT DEVICES

BACKGROUND OF THE INVENTION

1. Field of the Invention

The present invention relates to apparatuses for differentiating blood vessel type in the vascular access field.

2. Prior Art

In medicine numerous vascular access procedures are carried out for placement of needles, catheters, guidewires into blood vessels for a variety of indications and procedures. Arteries and veins are accessed for various and different reasons. Veins are usually accessed for administration of fluids, drugs, blood and blood products, for angiographic studies of the venous system, venous pressure monitoring, blood sampling and others. Arteries are accessed for invasive blood pressure monitoring, delivery of specific drugs at specific locations, angiographic studies, blood sampling for blood gas analysis, interventional cardiological procedures and others.

Except for the superficial suprafascial veins which run alone without the correspondent artery, deep blood vessels, arteries and veins run in most cases alongside with each other, vasa concomitantes, and have the same name. Superficial veins are veins which run above the fascia beneath the skin, return blood from the skin and the subcutaneous regions into the deep veins. In most cases superficial veins are visible under the skin and palpable. These are the veins commonly accessed by health care operators for blood sampling and for placement of intravenous lines.

Deep blood vessels, veins or arteries are anatomically deeply located and are neither visible nor palpable. Deep veins of the systemic circulation are called central veins and are used for vascular access for a variety of indications: rapid administration of fluids, medications, blood or blood product in situation of emergency such as cardiac arrest or shock in which most peripheral veins are collapsed, insertion of cardiac Swan-Ganz balloon catheters, failure to obtain vascular access by the peripheral route, measurement of central vein pressure, insertions of transvenous pacemakers, administration of hyperalimentation solutions and others.

The most common central veins used for gaining access to the circulation are the jugular vein, in the neck, the subclavian vein, beneath the collar bone, and the femoral vein, in the groin.

The procedure for gaining access to central veins and placing a catheter into a central vein is called central line placement. Usually it is carried out with the Seldinger technique which encompasses the insertion of a guidewire into a blood vessel prior to the insertion of a catheter. Regardless of the devices and the techniques used the blood vessel is accessed by the operator via a hollow needle. The operator aims at a target central blood vessel with a needle connected to a syringe or to a Guidewire Placement Device as disclosed by Zadini et al. in U.S. Pat. Nos. 5,415,177, 5,579780 and 5,749,371. Once the operator ascertains blood vessel penetration by visualizing blood flashback into the syringe or the vacuum chamber of the Guidewire Placement Device, the operator proceeds with the Seldinger technique of guidewire insertion. A guidewire is advanced through the hollow needle into the vessel lumen to a desired length. The needle is then removed, the guidewire is left in place within the vessel and a catheter with introducer is slid over the guidewire into the vessel and advanced into it.

Same procedure is carried out for gaining access to arteries.

Due to the fact that arteries and veins run alongside, it is often difficult for the operator to differentiate whether an artery or a vein has been penetrated by the needle tip.

Color of the blood, usually darker in veins, pulsatility of the blood absent in venous blood and present in arterial blood, can help the operator in distinguishing between the two. However no known method or apparatus gives the operator the absolute certainty that a vein has been penetrated instead of an artery.

Placing a catheter in the wrong type of vessel can carry disastrous consequences to a patient, causing significant morbidity and, at times, mortality. Furthermore in carrying out the procedure of central line placement in subclavian or internal jugular veins, the pleura and the lungs can be punctured accidentally by the operator with the needle and the catheter can be erroneously advanced into the pleural cavity. This can result in the dreadful complications of pneumothorax, hemothorax and/or hydrothorax.

It is therefore of paramount importance for the operator "to know where is at with its needle", whether in a vein, artery or pleural cavity, before completing the procedure of guidewire advancement and catheter placement.

Fischell et al. disclose in their U.S. Pat. No. 5,242,414 an "ergonomic vascular access needle" device which allows insertion of a guidewire through a lumen of a plunger of the device into a blood vessel . The device has a centrally located capillary tube in flow communication with a variable volume chamber. The volume of this variable volume chamber can be preset at some specific volumes, different for vein in respect to arteries. When this variable volume chamber is preset for arteries, blood pulsatility can be observed within the capillary tube confirming arterial cannulation instead of venous cannulation as arterial blood within the capillary tube generally pulsates while venous blood generally does not. While this device provide the operator with means of identification of blood vessel type penetration, still has definite drawbacks. First of all, at low pressures, such as pressures encountered often in clinical situations which demand insertion of central lines, the pulsatility of the arterial blood may be absent or hardly distinguishable from variation in length of the blood column which could occur with patient respiration in the venous central system. The method of blood vessel type identification by pulsatility is therefore unreliable as too often unpredictably dependent upon the clinical situation.

Marks discloses in its U.S. Pat. No. 5,314,410 an entry indicator for arterial or intravenous needles. The invention relates to a device basically composed of a hollow needle with transparent hub and a grossly dome shaped membrane with a flexible portion sealingly attached to the inside of the needle hub and covering the proximal portion of the needle. According to the inventor the flexible portion of the membrane may move or inflate in response to pressure within the blood vessel penetrated by the needle tip.

This device has obvious drawbacks and limitations. The device cannot be used with syringes of any type nor guidewire placement devices. Indeed the disclosed device can be used only with catheters over the needle as the membrane attached to the hub and covering the proximal portion of the needle precludes any use of syringes, guidewires, catheters inside the needle as the membrane completely blocks the patency to passageway of the needle.

Furthermore Marks in the cited U.S. Pat. No. 5,314,410 in the paragraph "Background of the invention" states that "the present intravenous and arterial cannulas depend upon a visual observance of blood itself in the hub of the cannula after the blood has flowed trough the length of the cannula in order to indicate that the cannula needle has entered the vessel".

It is obvious that, in the device disclosed by Marks, it is the column of air within the cannula which displaces the flexible portion of the membrane upon blood vessel penetration by the needle tip serving as indicator of blood vessel penetration. Otherwise, should be the blood to deflect the flexible portion of the membrane, the device would be neither useful nor novel as the operator would visualize the blood at the proximal end of the needle well before the flexible portion of the membrane flexes in response to the fluid pressure of the blood.

It is seems obvious that the column of air, capable of stretching the flexible portion of the membrane to the extent disclosed, illustrated and claimed in the Mark's Patent requires a certain degree of compression prior to the stretching of the flexible portion of the membrane. This compression of air may delays the indication of blood vessel penetration by the needle tip and may make Mark's device unreliable in clinical situations of low blood pressure where the column of air is expected to be only marginally compressed.

A search in the Patent office failed to identify any apparatus for syringes or guidewires placement devices or in general for vascular access devices provided with vacuum creating means, capable of achieving blood vessel type differentiation rapidly, swiftly and reliably at bedside as the invention below disclosed.

SUMMARY OF THE INVENTION

The disadvantages of the present equipment and methods of central line placement into the blood vessels, equipment and methods with which the operators are unable to differentiate penetration of vessel types and pleural cavity are overcome with the present invention.

A blood vessel type differentiator for syringes and guidewires placement devices is proposed capable of differentiating blood vessel type and pleural cavity penetration by the needle tip with a simple effective visual means of identification by means of detecting blood pressure difference between vessels. Blood pressure within arteries and veins differs significantly and consistently even in clinical conditions of extremely low arterial blood pressure such as in shock, hypovolemic, cardiogenic or neurogenic. The difference between arterial pressure and venous pressure is indeed significant, usually varying several mm of Hg, in physiological and pathological conditions. In peripheral veins used for IV access the average blood pressure is 4 to 8 mm of Hg. the mean being 7.1. Central vein pressure is even, lower: the mean central vein pressure is 4.1 mm of Hg.

Arterial pressure is much higher than vein pressure even in situation of significant low arterial pressure such as the pressures encountered in patients in shock. In normotensive patients (blood pressure 140/90) the mean blood pressure is 106 mm of Hg. Please refer for instance to the Table "Blood pressure levels in different portions of the circulatory system in Gayton A C : Textbook of medical physiology, Philadelphia, 1991, W B Saunders.

With the present invention the inventors propose a blood vessel type differentiator incorporated within vascular access devices provided with vacuum creating means such as syringes and guidewire placement devices.

The device generally comprises a piston plunger sealingly and slideably mounted within a vacuum chamber in flow communication with a needle, such as the vacuum chambers of syringes and guidewire placement devices, said plunger being movable against a pressure sensitive spring, or pressure sensitive resilient means, to serve the dual purpose of A) creating the vacuum within the vacuum chamber and B)of indicating the type of the anatomical cavity penetrated by the needle to the operator, if vein, artery or pleural cavity by its positioning within the vacuum chamber in respect to a reference tab.

In summary as soon as the needle tip penetrates the vessel wall, blood aspirated by the plunger or piston enters the needle tip and travels through to the hollow needle into the vacuum chamber up to the piston head. As soon as the blood aspirating stage is completed the piston plunger is urged posteriorly by the fluid pressure of the blood. A calibrated sensitive spring opposes the posterior displacement of the piston by the blood pressure. The pressure of the blood within the vacuum chamber urges and displaces the piston urged backwardly of an amount resulting from the difference between the pressure of the blood present in the penetrated vessel and transferred into the vacuum chamber and the opposing force of the calibrated spring which urges the piston forwardly.

In other types of embodiments a movable pressure sensitive member such as a piston is sealingly and slideably mounted within a chamber in flow communication with a vacuum chamber where vacuum is created by vacuum creating means such as a piston plunger. In these embodiments as in the embodiments where the movable pressure sensitive member also acts as a vacuum creating means, the movable pressure sensitive member operates within a vacuum environment where the vacuum is not created but transferred from the adjacent vacuum creating chamber and is backwardly displaced against a pressure sensitive resilient means such as a spring upon establishment of positive pressure in the vacuum chamber by entry of the blood into the vacuum chamber.

The piston plunger position within the vacuum chamber in respect to a reference point tab, indicates the type of anatomical cavity penetrated by the needle to the operator. In the event of arterial penetration, due to the higher pressure in arteries than in veins, the piston is further backwardly displaced.

In other embodiments the visual indicator is a color coded piston visible through a transparent wall area or through a windows. Blue color can be used for the veins, red for the arteries and yellow for the pleural cavity while white for the device at rest prior to use.

The advantages of such devices are self-explanatory. The device provides the operator with a simple means of detecting vessel type upon blood vessel penetration by the needle tip in all kind of devices provided with vacuum creating means, such as syringes, etc. The operator just by looking at the position of the piston plunger in respect to a reference tab on the device, or at the color indicator, knows exactly where the needle tip has been placed, whether within an artery, a vein or the pleural cavity.

It is an object of the present invention to provide physicians, nurses and health care operators in general with a simple, easy to operate device that can effectively assist the operator during the procedure of blood vessel catheterization via syringes or guidewire placement devices by providing the operator with a simple visual indicator of anatomical cavity penetration.

The device has all the prerequisites of reducing morbidity and mortality by enabling the operator to differentiate between blood vessel type and pleural cavity at bedside prior to the insertion of guidewires or catheters into the desired blood vessel.

DRAWING FIGURES

FIG. 2 is a cross sectional view of the device of FIG. 1 upon vacuum creation after skin penetration by the needle tip with the piston/plunger indicator still in a neutral position.

FIG. 3 is a cross sectional view of the device of FIG. 1 indicating that a blood vessel has been penetrated by the needle tip.

FIG. 4 is a cross sectional view of the device of FIG. 1 indicating that a vein has been penetrated by the needle tip.

FIG. 5 is a cross sectional view of the device of FIG. 1 indicating that a vein with higher pressure than in the vein of FIG. 4 has been penetrated by the needle tip.

FIG. 6 is a cross sectional view of the device of FIG. 1 indicating that an artery has been penetrated by the needle tip.

Figure 1:
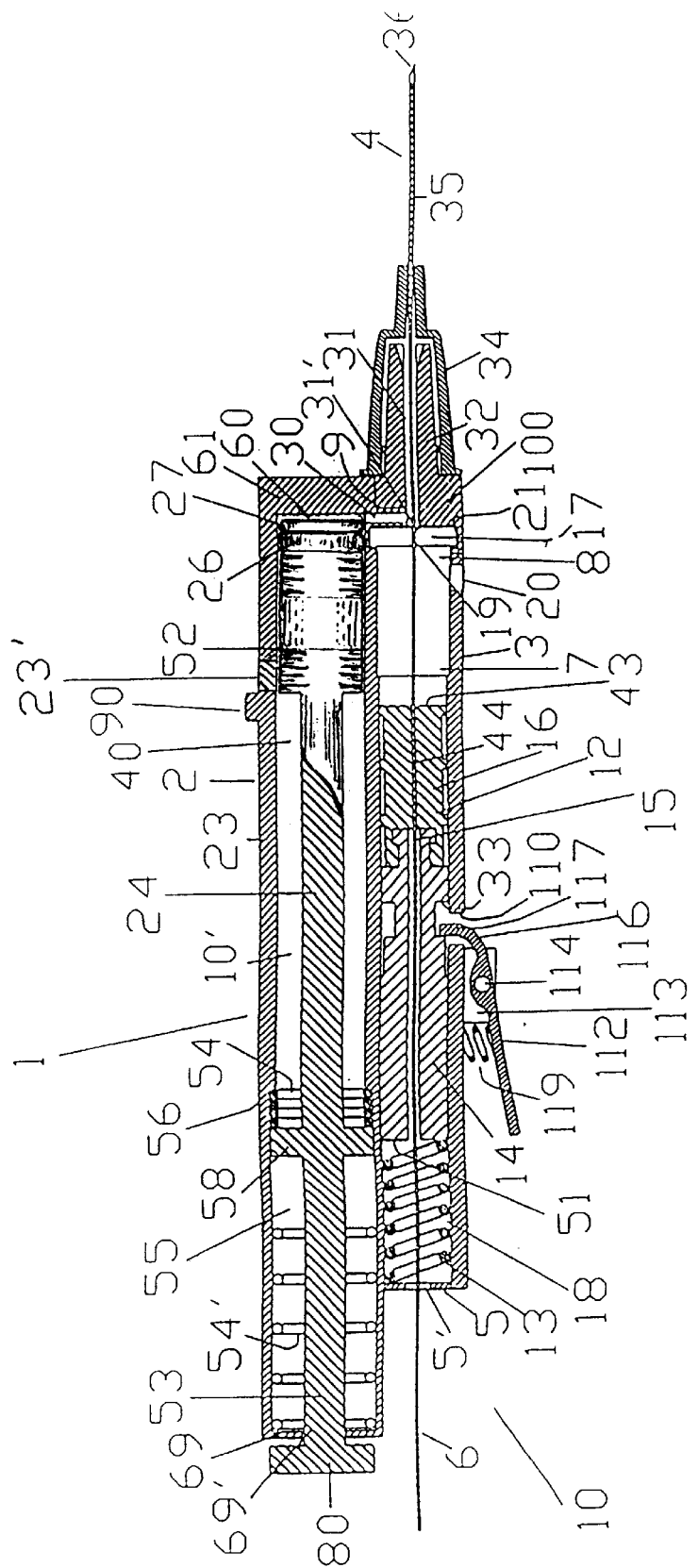
FIG. 1 is a cross sectional view of the blood vessel type differentiator incorporated within a guidewire placement device, shown at rest prior to use, with the piston/plunger indicator in neutral position.
Figure 7:
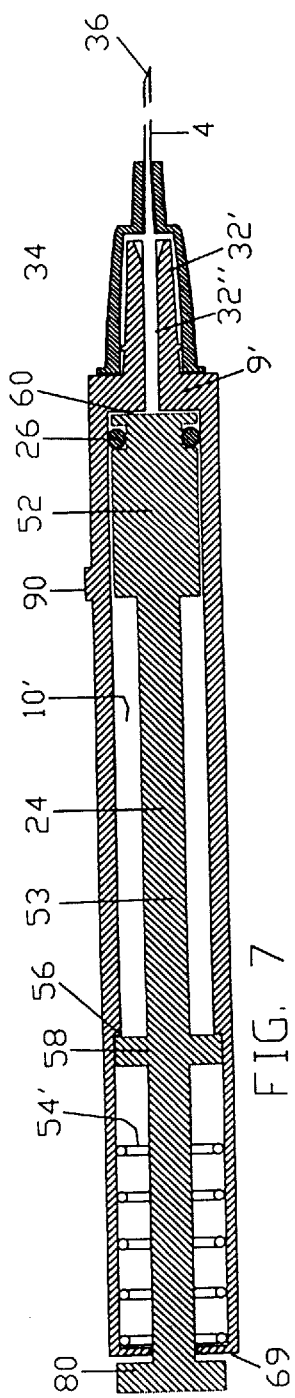

FIG. 7. is a cross sectional view of another version of the device of FIG. 1 incorporated within an ordinary syringe with manual plunger.

Figure 8:
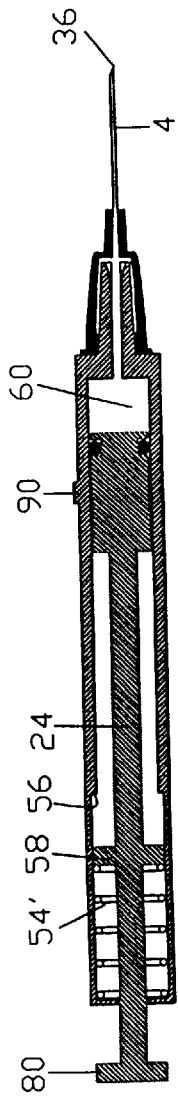

FIG. 8 is a cross sectional view of the device of FIG. 7 at a different stage of operation, upon vacuum creation after skin penetration by the needle tip.

Figure 9:
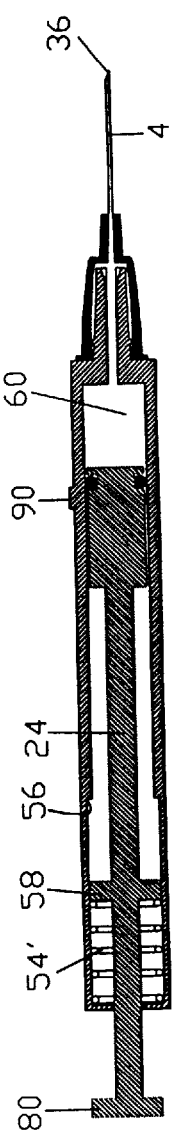

FIG. 9 is a cross sectional view of the device of FIG. 7 indicating that a vein has been penetrated by the needle tip.

Figure 10:
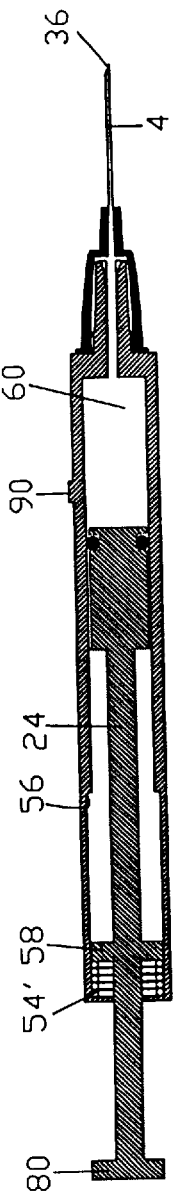

FIG. 10 is a cross sectional view of the device of FIG. 7 indicating that an artery has been penetrated by the needle tip.

Figure 11:
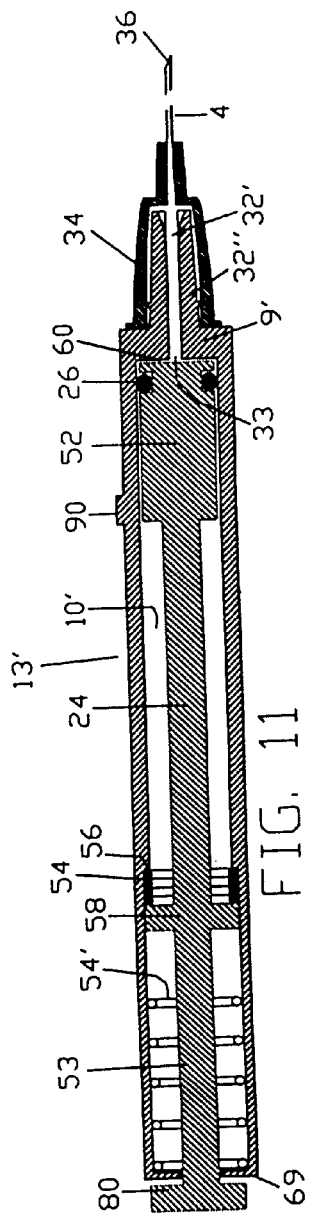

FIG. 11 is a cross sectional view of another version of the device of FIG. 1 incorporated within a syringe where the piston-plunger creating the vacuum is rearwardly displaced by a spring.

Figure 12:
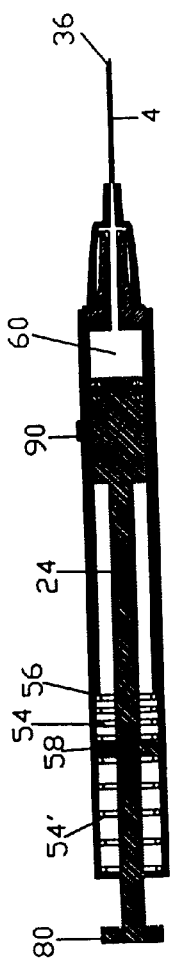

FIG. 12 is a cross sectional view of the device of FIG. 11 at a different stage of operation, upon vacuum creation, after skin penetration by the needle tip.

Figure 13:
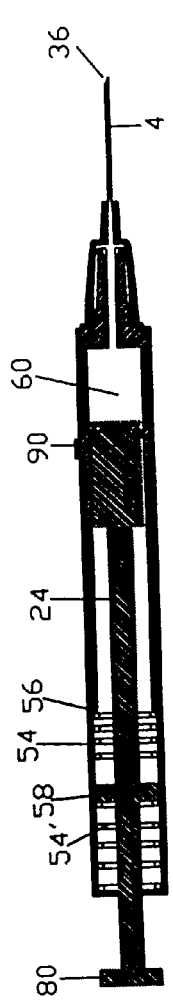

FIG. 13 is a cross sectional view of the device of FIG. 11 indicating that a vein has been penetrated by the needle tip.

Figure 14:
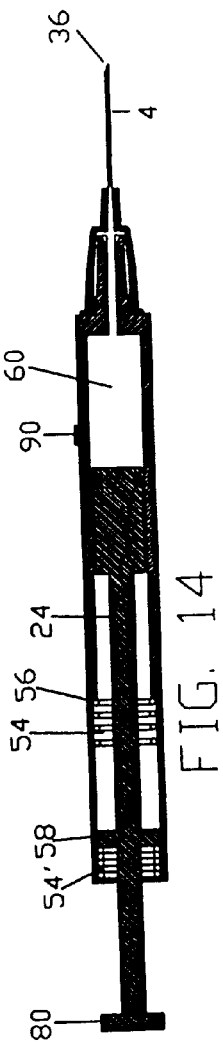

FIG. 14 is a cross sectional view of the device of FIG. 11 indicating that an artery has been penetrated by the needle tip.

FIG. 15 is a cross sectional view of another version of the device of FIG. 1 where the vacuum creating means is a resilient bellow.

FIG. 16 is a cross sectional view of the device of FIG. 15 at a different stage of operation, upon vacuum creation, after skin penetration by the needle tip.

FIG. 17 is a cross sectional view of the device of FIG. 15 indicating that a vein has been penetrated by the needle tip.

FIG. 18 is a cross sectional view of the device of FIG. 15 indicating that an artery has been penetrated by the needle tip.

FIG. 19 is a cross sectional view of the device of FIG. 15 applied to a T connector.

FIG. 20 is a cross sectional view of the device of FIG. 15 applied to the T connector, upon vacuum creation after skin penetration by the needle tip but prior to blood vessel penetration.

FIG. 21 is a cross sectional version of the device of FIG. 15 applied to a T connector indicating that a vein has been penetrated by the needle tip.

FIG. 22 is a cross sectional view of the device of FIG. 15 applied to a T connector indicating that an artery has been penetrated by the needle tip.

Figure 23:
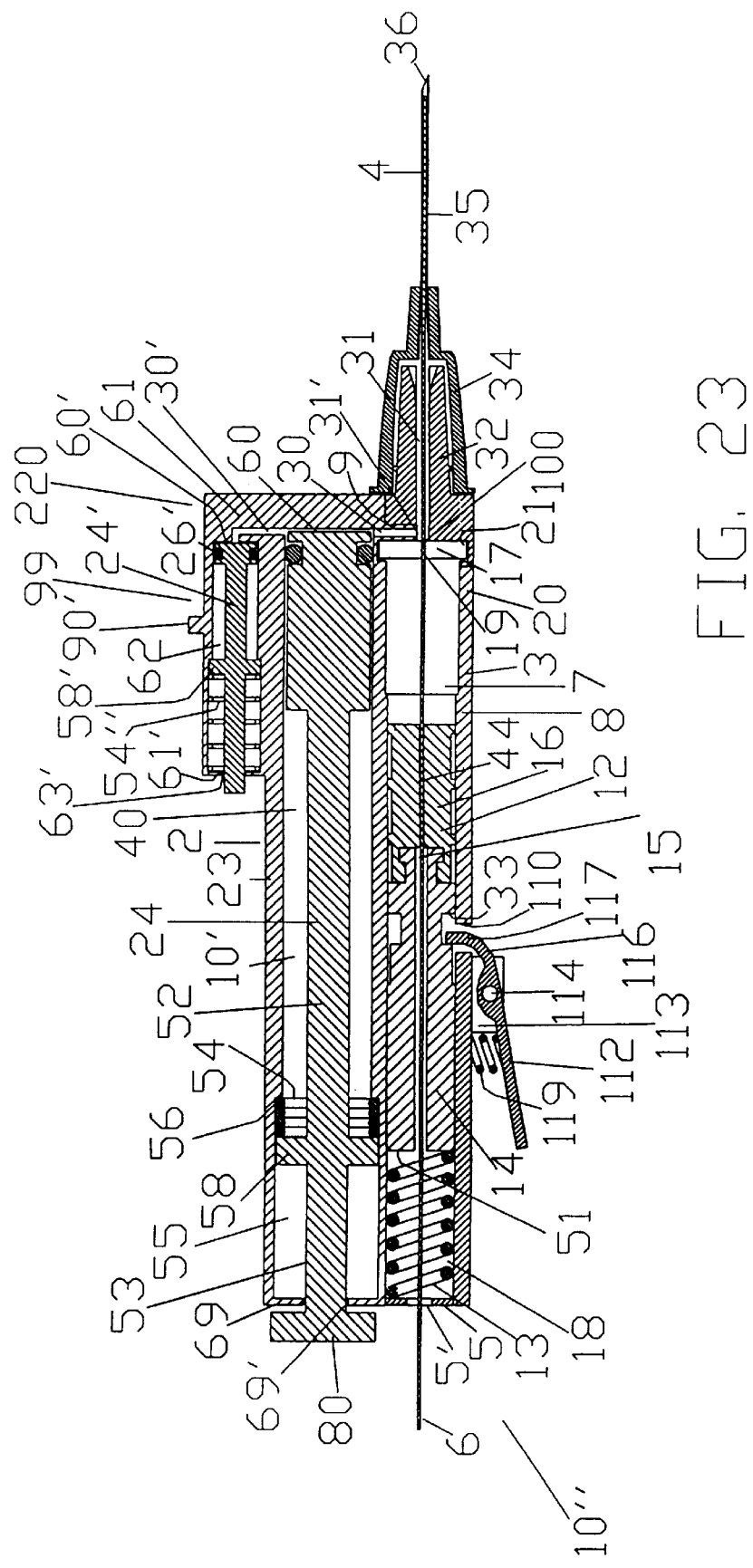

FIG. 23 is a cross sectional view of another version of the blood vessel type differentiator of FIG. 1 incorporated within a guidewire placement device.

FIG. 24 is a cross sectional view of another version of the blood vessel type differentiator incorporated within a Raulerson syringe.

FIG. 25 is a cross sectional view of another version of the blood vessel type differentiator added to a Raulerson syringe.

DETAILED DESCRIPTION OF THE DEVICE

FIG. 1 shows the automatic blood vessel type differentiator incorporated within a guidewire placement device. Guidewire placement devices have been described by Zadini et al in U.S. Pat. Nos. 5,415,177, 5,579780 and 5,749,371. These devices are capable of inserting medical guidewires into blood vessels upon and in response to blood vessel penetration by a needle tip. The blood vessel type differentiator is incorporated or added in the semiautomatic and manual version of the guidewire placement devices. The semiautomatic versions of the guidewire placement devices have been fully disclosed in U.S. Pat. No. 5,415,177 pages 12 FIGS. 18,18A, and U.S. Pat. No. 5,749,371, FIGS. 8,9,10,11, page 9 through 11. The manual versions of the guidewire placement device has been disclosed in U.S. Pat. No 5,579,780.

As shown in FIG. 1, the differentiator, generally indicated at 1, described below, is incorporated within a semiautomatic guidewire placement device. More precisely differentiator 1 is incorporated within the upper chamber or vacuum chamber or syringe chamber or differentiator chamber indicated at 10' of a guidewire placement device.

The semiautomatic guidewire placement device disclosed below in FIGS. 1 to 6, indicated at 10, is very much similar to device 1" of FIG. 11 disclosed in pages 10 and 11 of U.S. Pat. No. 5,749,371, except for minor structural changes for adaptation of differentiator 1.

The guidewire placement device indicated at 10 is composed of a housing, indicated at 2, which is essentially formed with two generally parallel barrels or chambers of generally cylindrical shape: upper chamber or vacuum chamber 10' where differentiator 1 is incorporated, and lower chamber or guidewire chamber 8. To device 10 is connected to needle 4. The differentiator is generally composed of a vacuum chamber, a piston slideably mounted in it and a pressure sensitive spring. Vacuum chamber or differentiator chamber 10' of general cylindrical shape is delimited laterally by side wall 23, anteriorly by anterior wall 61, posteriorly by wall 69. Vacuum chamber wall 23 is transparent at least anteriorly in order to visualize the position of the piston 24 within vacuum chamber 10'. Side wall 23 of vacuum chamber 10' is formed superiorly with reference point or mark or tab 90. Posterior wall 69 has opening 69' for the passage of posterior segment 53 of piston plunger 24 as it will be apparent from the description below.

Vacuum chamber 10' is composed of two segments, an anterior segment 40 and a posterior segment 55. The two segments are concentric and posterior segment 55 is of greater diameter than anterior segment 40. Annular flange 58 separates the two segments.

Within vacuum chamber 10', vacuum creating means or piston 24 is mounted in slideable fashion. Piston 24 is composed of anterior segment 52 having front end 43 and posterior segment 53 separated by flange 56. Posterior piston segment 53 has handle 80 at the rear end . Piston 24 is urged backwardly by spring 54 which encircles anterior piston segment 52 and seats in posterior segment 55 of vacuum chamber 10' between flange 58 of vacuum chamber 10' and flange 56 of piston 24. Calibrated sensitive spring 54' encircles posterior piston segment 53 seating on posterior wall 69 of vacuum chamber 10' and is a component of the differentiator.

Piston 24 has sealing O-ring 26 seating on annular recess 27, to provide sealing between vacuum creating means or piston 24 and lateral wall 23 of vacuum chamber 10'. Space 60 is the space within chamber 10' in front of anterior piston segment 52.

Piston 24 can be color coded in sequential segments, each colored segment to indicate the different anatomical cavity penetrated by the needle, for instance bleu for veins, red for arteries, white for the resting position of the piston, yellow for the pleural cavity. In embodiments with color coded piston, wall 23 is better constructed of non transparent material except for a small window 23' or area which permits visualization of a single segment of color coded piston 24.

Vacuum chamber 10' is in flow communication with hollow needle 4 via conduit 30 formed within anterior wall 9 of guidewire chamber 8 and passageway 31 of hub 32 of device 10.

Guidewire chamber 8 is in all identical to guidewire chamber 8 of device 1" of FIG. 11 disclosed in pages 10 and 11 of U.S. Pat. No. 5,749,371. Guidewire chamber 8 is for convenience here below re-described. Guidewire chamber 8 of general cylindrical shape has sidewall 3 and it is closed anteriorly by anterior wall 9 and posteriorly by posterior wall 5. Anterior wall 9 has opening 31' in communication with passageway 31 within hub 32 of device 10. Anterior wall 9 is also formed with conduit 30 in flow communication with passageway 31 of device hub 32 as above described. Posterior wall 5 also has an opening, indicated at 5', to allow passage of guidewire 6. Guidewire chamber 8, as vacuum chamber 30', is made of two segments, an anterior segment, indicated at 7, and a posterior segment, indicated at 18. The two segments are concentric but anterior segment 7 is of greater diameter than posterior segment 18.

Within guidewire chamber 8, guidewire piston 12 is slideably mounted. Guidewire piston 12 is composed of a posterior segment 14 and anterior segment, or guidewire introducer, 16, made of resilient compressible /expandable material such as rubber. Guidewire introducer 16 could also be designed as a mandrin or as a chuck. As described in above cited patents, the elements of the mandrin or chuck may have uneven or rough internal surface to reduce the chance for sliding of the guidewire with respect to the mandrin or to the chuck when gripping the guidewire.

Spring or resilient means 13 is mounted within posterior chamber segment 18, rear of posterior piston segment 14 of piston 12, and seats between posterior face 51 of posterior piston segment 14 of piston 12 and posterior wall 5 of guidewire chamber 8.

Posterior segment 14 of guidewire piston 12 has at its center axial tract 15 for guidewire 6 which is mounted in a slideable fashion within axial tract 15. Guidewire introducer 16 which is in position of rest prior to use, is compressed within posterior narrower chamber 18, and, by such compression, tightens in a gripping fashion around guidewire 6 which is mounted within passageway 44 of guidewire introducer 16.

Sealing member or sealing means 17 is sealingly engaged to, and seats on, annular recess 21 formed within anterior wall 9 of guidewire chamber 8 and provides sealing around guidewire 6 within passageway 19 located at the center of sealing member or means 17. Guidewire 6, although, as pointed out above, is sealingly engaged to sealing member 17, remains slideable along passageway 19 of sealing member or means 17.

For the purpose of obtaining a sealing, between guidewire 6 and sealing member 17, capable of being maintained indefinitely or reliably for the time required to locate the vessel even in cases when such time is extended for difficulties in locating the vessel, guidewire 6 is modified in segment 100. Modified segment 100 of guidewire 6 is cylindrical with an outer diameter which is about the same as the outer diameter of guidewire 6, the cylindrical segment being interiorly closed to passage of air, and has a substantially even surface for sealingly slideably engaging the sealing member 17 of vacuum chamber 8. As disclosed in above cited patents the segment of the guidewire which is engaged with sealing member 17 can be modified in a number of ways to attain the same results of maintaining a sealing engagement between guidewire 6 and sealing member 17 and adequate slideability of guidewire 6 with respect to sealing member 17.

Window 20 in device 1 is formed inferiorly and anteriorly in wall 3 of anterior segment 7 of guidewire chamber 8 to permit the exit of air from anterior segment 7 of guidewire chamber 8 during the operation. Lever or trigger or actuator 112 is mounted on mounting bracket 113 via pin 114. Lever 112 has front curved arm 116 for entry into opening 110 on inferior side wall 3 of guidewire chamber 8, has tooth 117 for engagement with annular recess 33 of guidewire piston 12, and has rear arm 115 for lever actuation by the operator. Lever 112 is tilted forwardly by spring 119 to engage annular recess 33 of piston 12 with tooth 117.

Guidewire 6 is slideably mounted, from front to back, within the lumen of hollow needle 4, passageway 31, opening 31' on anterior wall 9 of guidewire chamber 8, passageway 19 within sealing member or means 17, passageway 44 of guidewire introducer 16, axial tract 15 of piston 12 and exits posteriorly from posterior end 51 of piston 12 and finally through opening 5' of posterior wall 5 of guidewire chamber 8. Opening 31', passageway 19 passageway 44, axial tract 15, opening 5' are cooperatively patency means.

Housing 2 of device 10 is formed at its front lower end with hub 32 having at its center passageway 31. Needle hub 34 seats circumferentially on hub 32 of device 10. Needle or cannula 4 is composed of needle shaft 35, needle hub 34, connected as just described to hub 32 of device 10, and needle tip 36.

Description of the Operation

In FIG. 1 the blood vessel type differentiator 1, incorporated within semiautomatic guidewire placement device 10 is shown armed prior to skin insertion of needle tip 36 of needle 4. Piston plunger 24 has been fully advanced by the operator by acting on handle 80. Spring 54 is compressed between flange 56 and flange 58.

As shown in FIG. 2 after penetration of skin 105 with needle tip 36, the operator releases his or her grip on handle 80 releasing piston 24 . Piston 24 is displaced posteriorly by uncoiling of spring 54. Vacuum is created in space 60 of vacuum chamber 10' in front of piston 24. Posterior displacement of piston 24 will be only of a small amount due to the sealing of needle tip 36 by subcutaneous tissue 108.

At this point the operator will search for a suitable vessel underneath skin 105 with needle tip 36 of needle 4.

As shown in FIG. 3 as soon as needle tip 36 penetrates blood vessel 107, by perforating its wall 106, blood backflow will occur in an accelerated fashion in space 60 of vacuum chamber 10' in front of piston 24, blood rushing into space 60 passing from the needle through passageway 31 and conduit 30.

Piston 24 no longer retained by the vacuum which has vanished upon blood vessel penetration by needle tip 36 will move rearwardly urged by spring 54.

If pleural cavity rather than a blood vessel is penetrated by needle tip 36, no blood will be visualized in space 60. However, piston 24 will move either forward or backward depending upon which negative pressure is prevalent, the negative pressure of the pleural space or the negative pressure of the vacuum within vacuum chamber 10'.

FIG. 4 shows the device indicating a venous blood vessel penetration by needle tip 36. Piston 24 continues to move backwardly, after compression spring 54 has become inactive by regaining its fully extended position and no longer urges piston 24 rearwardly, due to the pressure of the blood which has entered space 60 of vacuum chamber 10' in front of piston 24. Pressure sensitive calibrated spring 54' opposes resistance to such pressure exerted by the blood entered in space 60 in front of piston 24. Upon vein penetration, front end 43 of piston 24 stops forwardly of reference tab 90 of vacuum chamber 10'.

FIG. 5 shows another example of venous penetration where the venous pressure is higher and the front end 43 of piston 24 is aligned with reference tab 90.

FIG. 6 shows arterial penetration by the needle with piston 24 further displaced posteriorly in respect to reference tab 90 against opposing calibrated sensitive spring 54' due to the fact that arterial pressure is consistently higher than venous pressure.

Once the operator has ascertained blood vessel type penetration by looking at the position of front end 43 of piston 24 in respect to tab 90, he or she will advance guidewire 6 into the blood vessel by acting on trigger 112 or will withdraw the device and abandon the procedure if the needle will not be found in the desired blood vessel.

In FIG. 7 through 10 the differentiator, generally indicated at 12', is incorporated within an ordinary syringe rather than within a semiautomatic guidewire placement device. The syringe incorporating the blood vessel type differentiator can be used for guidewire insertion into blood vessels or used for other purposes.

The differentiator-syringe 12' is in all similar to the differentiator-syringe 1 of guidewire placement device 10 of FIGS. 1 to 6 except for few difference outlined below. Reference numbers illustrating the same components have being maintained. Piston 24' is withdrawn manually. Spring 54 is no longer present.

Anterior wall 9' of vacuum chamber 10' is formed with hub 32' or means for releasably connecting vacuum chamber 10' to cannula 4 or patency means between chamber 10' and cannula 4. Hub 32' is formed at its center with passageway 32" in flow communication with space 60 in front of piston 24 via opening 33.

In use, the operator prior to skin insertion of needle 4 fully advances piston 24, then, after inserting needle tip 36 into the skin, withdraws plunger 24 manually. As shown in FIG. 8 the operator will sense resistance to the withdrawing action by the vacuum created in front of piston 24 in space 60 due to the sealing of the needle tip by the subcutaneous tissues. Upon blood vessel entry, blood will rush into space 60 and the operator releases piston 24 allowing blood pressure to displace piston 24 against pressure sensitive spring 54'. As shown in FIG. 9, if front end 43 of piston 24 stops in front of reference tab 90 the needle tip is acknowledged being in a vein.

As shown in FIG. 10 if front end of piston 24 stops rearwardly of tab 90 then the needle tip is acknowledged being in an artery.

FIGS. 11 to 14 show the differentiator generally indicated at 13' in all similar to the differentiator-syringe 12' of FIGS. 7 to 10 except that withdrawing of piston 24 as for device 1 of FIGS. 1 trough 6 is accomplished by resilient means or spring 54. Spring 54 as for device 1 of FIGS. 1 through 6 seats between flange 56 of piston 24 and flange 58 of chamber 10'.

In use the operator arms the device by exerting forward pressure upon plunger 24 to forwardly displace piston 24 to its full forward position. The operator than inserts needle 4 into the skin. Plunger 24 displaced posteriorly by spring 54 will create a vacuum in space 60. As shown in FIG. 12, displacement of piston 24 will be limited by the vacuum being created. Upon entry into a blood vessel, blood will enter into chamber 60 in front of piston 24. The blood pressure will displace piston 24 rearwardly against sensitive spring 54'. As shown in FIG. 13 if front end 43 piston 24 stops in front of reference tab 90 a vein has been penetrated. As shown in FIG. 14 if front end 43 of piston 24 stops rearwardly of tab 90 the needle has entered an artery.

FIGS. 15 through 18 shows an alternative form the differentiator-syringe of FIGS. 1 to 6.

As shown in FIG. 15 this device generally indicated at 200 is composed of chamber 201 where is slideably mounted plunger 204 having handle 206 body 208 and head 210. Resilient bellow 212 which is sealingly connected to opening 203 of passageway 205 of hub 215 in flow communication with hollow needle 4, is attached to plunger head 210. Pressure sensitive calibrated spring 216 seats on posterior wall 211 of chamber 201 and encircles body plunger 208. Resilient bellow 212 urges piston 204 rearwardly when the device is armed by pressing fully forward piston 204 as shown in FIG. 15.

Side wall 207 of syringe barrel 201 is formed with reference tab 209 while posterior wall 211 is formed with opening 214 for the passage of body 208 of plunger 204. FIG. 15 shows the device armed ready to be used after full advancement of piston 204 resulting in compression of resilient bellow 212 by the operator.

FIG. 16 is a cross section of the device after skin penetration with the resilient bellow creating vacuum in its interior 202 by resiliently extending itself rearwarly by a limited amount due to the skin sealing of needle tip 36.

FIG. 17 shows the device after vein penetration, precisely penetration of a vein. Blood pressure urges resilient bellow 212 rearwardly, concurrently with plunger 204 against pressure sensitive spring 216. Plunger head 210 stops in front of tab 209 indicating that the needle tip is in a vein.

FIG. 18 shows the device after artery penetration. Piston head 210 stops rearwardly in respect to reference tab 209 as the blood pressure in an artery is greater than in a vein.

Resilient bellow 212 can be substituted by a membrane preferably dome shaped rearwardly displaceable by spring adjacent to the membrane to function as a vacuum creating member as resilient bellow 212. Upon entry of blood in to the chamber where the vacuum is created by the membrane, the membrane is further displaced rearwardly by the blood pressure against the pressure sensitive spring of the type indicated with numeral 216 in FIGS. 15 through 18.

FIGS. 19 through 22 show differentiator 200 of FIGS. 15 through 18, in use with a connector used in the vascular access field, in this case a T shaped connector. T shaped connector has three arms, anterior arm 250 to which is connected needle 4, superior arm 251 connected to hub 215 of differentiator 200 and posterior arm 252 open for connection to syringes, I.V. tubing or the likes. In FIG. 19 device 200 is armed by the hand of the operator who fully advances plunger 204 to compress bellow 212 forward and concurrently the operator seals the hub of arm 252 of the T connector with his or her finger in order to prevent entry of air.

FIG. 20 shows the device after skin penetration prior to blood vessel penetration. Operator releases his finger pressure on plunger 204. Bellow 212 resiliently extends rearwardly by a limited amount due to the skin sealing of needle tip 36.

As described for FIG. 17, FIG. 21 shows device 200 when a vein has been penetrated by the tip of the needle.

As described for FIG. 18, FIG. 22 shows device 200 when an artery has been penetrated by the tip of the needle.

FIG. 23 shows an alternative version of the device of FIGS. 1 through 6 being applied to a guidewire placement device here generally indicated at 10". The differentiator, generally indicated at 220, is added on, in a piggy back fashion and anteriorly, to vacuum chamber 10'. Guidewire placement device 10" is in all similar to guidewire placement device 10 of FIGS. 1 to 6 except for very few structural differences. Spring 54' is no longer present.

Differentiator 220 is composed of vacuum chamber 62 where is slideably mounted piston 24' which is provided at its front end with O-ring 26'. Vacuum chamber 62 has side wall 99, anterior wall 61 and posterior wall 61' which is formed with opening 63' for passage of the posterior segment of piston 24'. Piston 24' is formed with flange 58'. Spring 54" is positioned posteriorly in vacuum chamber 62 seating on posterior wall 61', encircling the posterior segment of piston 24'. Side wall 99 is formed with reference tab 90'. Space 60' in front of piston 24' is in flow communication with space 60 of vacuum chamber 10' via conduit 30'.

The device is used as device 10 of FIGS. 1 to 6. The operator fully advances plunger 24 within vacuum chamber 10'. After the skin has been penetrated by needle tip 4, the operator releases piston-plunger 24. Vacuum is created in space 60 by posterior displacement of piston 24 by spring 54 and transferred into space 60' in front of piston 24' of differentiator 220, being space 60' in flow communication with space 60 of vacuum chamber 10' via conduit 30'. As soon as a blood vessel is penetrated by needle tip 36, blood is aspirated into space 60 and 60'. The pressure of the blood within differentiator chamber 62 will displace rearwardly piston 24' against the opposing force of pressure sensitive spring 54". Depending upon where piston 24' stops in reference of tab 90, in front or rear of it, the operator will be able to detect the type of blood vessel penetrated by the needle, whether an artery or a vein.

FIG. 24 is a cross sectional view of the blood pressure type differentiator of FIGS. 1 to 6 being incorporated within a Raulerson syringe. Raulerson in his U.S. Pat. Nos. 4,813, 938 and 5,045,065 discloses a catheter introduction syringe for insertion of a guidewire into blood vessels, comprising a syringe barrel having a tip supporting a needle and a plunger slideably movable within the barrel, the front wall of the barrel supporting a rigid hollow cylindrical body. The plunger has a conduit longitudinally disposed within the plunger to permit the plunger to slide over the hollow cylindrical body. The conduit within the plunger leads to a valve assembly housed within the plunger which allows aspiration and flushing as an ordinary syringe and has the capability of allowing the passage of a guidewire through the valve assembly itself With minor structural changes and the incorporation of a pressure sensitive spring and a reference tab the Raulerson syringe is capable of differentiating type of blood vessel penetrated by the needle connected to it.

More in details, as shown in FIG. 24 the Raulerson syringe with incorporated differentiator generally indicated as 300, is composed of a syringe barrel 364 having front wall 309 and rear wall 369 delimiting vacuum chamber 310. Front wall 309 is formed with a hub 332 which has passageway 331. An ordinary needle 4 is connected with its hub 34 to hub 332 of device 300. Front wall 309 of barrel 364 and hub 332 supports rigid hollow cylindrical body 337 along its central longitudinal axis. Rigid hollow cylindrical body 337 is in flow communication with hollow needle 4 and also in communication with vacuum chamber 310 via opening 315 adjacent to anterior wall 309. Plunger 324 has conduit 370 longitudinally disposed within plunger 324 to slideably house hollow cylindrical body 370. Plunger 324 houses valve assembly 371. As shown in FIG. 24, valve 371 becomes in close proximity of the proximal end of cylindrical body 337 when plunger 324 is fully forwardly advanced. Valve 371 allows blood aspiration and flushing in the Raulerson syringe as in any ordinary syringe and has the capability of allowing the passage of a guidewire through the valve assembly itself.

To incorporate the vessel type differentiator the Raulerson syringe has the following structural changes. Syringe barrel 364 is formed with vacuum chamber 310 and posterior chamber 310' separated by annular flange 356. Plunger 324 is composed of anterior segment 352 and posterior segment 353 separated by plunger flange 358. Anterior segment 352 has plunger head 325 to which perforated sealing cap 326 is adapted. Within posterior chamber 310' is housed pressure sensitive spring or resilient means 354 which is seating on posterior wall 369 of syringe barrel 364 and encircles posterior plunger segment 353. Posterior wall 369 is formed with finger gripping flange 362 and with opening 368 for the passage of posterior plunger segment 353 which is provided with handle 380. Posterior plunger segment 353 is formed with passageway 361 from opening 363 on handle 380 up to valve 371 for passage of guidewires. Syringe barrel 364 is formed with reference tab 390 in its anterior segment.

Device 300 is used as an ordinary syringe. With piston plunger 324 fully advanced, the operator inserts needle tip 36 underneath the skin in search of a blood vessel. As for any ordinary syringe, plunger 324 is withdrawn by the operator. Valve 371 does not permit passage of air into vacuum chamber 310. As soon as a blood vessel is penetrated by needle tip 36, blood, aspirated by plunger 324, rushes into hollow cylindrical body 337 and through opening 315 into space 360 of vacuum chamber 310, in front of piston 324. Valve 371 does not permit passage of blood into passageway 361 of posterior piston segment 353. The operator, then, releases his or her grip on handle 380 allowing blood pressure to displace piston 324 rearwardly against sensitive spring 354. As for all devices previously described the position of the front end of piston plunger 324 in respect of reference tab 390 will indicate to the operator the type of vessel penetrated. If piston plunger front end 325 with sealing cap 324 stops in front of reference tab 390 a vein has been penetrated. If piston plunger front end 325 with sealing cap 324 stops rear of reference tab 390 an artery has been penetrated. The operator accordingly will or will not advance a medical guidewire through passageway 361, valve 371, hollow cylindrical body 337, hollow needle 4 up to needle tip 4 into the desired blood vessel.

FIG. 25 is a cross sectional view of a Raulerson syringe with the differentiator added on, rather than incorporated as in device 300 just described. This device is generally indicated at 300'. The added differentiator is exactly device 220 of FIG. 23.

The Raulerson syringe with differentiator 220 added on, is much similar to the Raulerson syringe of FIG. 24 except for few structural differences. Spring 354 is no longer present. Differentiator 220 is in flow communication with space 360 of vacuum chamber 310 of the Raulerson syringe in front of sealing cup 325 via conduit 30'.

The Raulerson syringe is used as the Raulerson syringe of FIG. 24. Differentiator 220 behaves exactly as in device 10" of FIG. 23. When blood is aspirated into space 60' by plunger 324 being withdrawn by the operator, the blood, beside rushing into space 360 will rush also in space 60 of differentiator 220 in front of piston 24'. As a result of the vacuum environment created also in chamber 62, the operator, as for device 10", will be able to "read" what type of vessel has been penetrated by needle tip 36 by looking at the position of the front end of piston 24' in respect of tab 390'.

What we claim is:

1. A device for differentiating type of blood vessel accessed by a cannula, for use in syringes and guidewire placement devices, comprising:
   (a) a first chamber in flow communication with the cannula;
   (b) a vacuum-producing member within the first chamber;
   (c) a pressure displaceable member, the pressure displaceable member being displaceable in response to venous and arterial pressure within the blood vessel accessed by the cannula;
   (d) a second chamber; and
   (e) a resilient member within the second chamber opposing the displacement of the pressure displaceable member.

2. The device of claim 1, wherein the second chamber is sealed from the first chamber by the pressure displaceable member.

3. The device of claim 2, wherein the first chamber has a transparent wall area adapted to allow visualization of the pressure displaceable member and a reference mark for reference of the pressure displaceable member's position in respect to the reference mark.

4. The device of claim 1, wherein the pressure displaceable member is within the second chamber.

5. The device of claim 1, wherein the resilient member comprises a calibrated spring.

6. The device of claim 1, wherein the pressure displaceable member is color coded by having colors in contiguous segments in a sequential fashion along its axis of displacement, each of said segments having a different color, and wherein the first chamber has a window to allow visualization of the color coded displaceable member.

7. The device of claim 1 wherein the pressure displaceable member is the vacuum producing member.

8. The device of claim 7, wherein the vacuum producing member is rearwardly displaceable from the cannula and comprises a handle adapted to be manually rearwardly displaceable to produce a vacuum within said first chamber.

9. The device of claim 7, further comprising a second resilient member urging the vacuum producing member rearwardly from the cannula.

10. The device of claim 9, wherein the second resilient member is within the first chamber.

11. The device of claim 7, wherein the vacuum producing member is a plunger.

12. The device of claim 7, wherein the vacuum producing member is a plunger having a conduit for insertion of guidewires through the plunger and a valve assembly along the conduit within the plunger to prevent air intake upon a rearward displacement of the plunger and to prevent blood leakage upon forward displacement of the plunger.

13. The device of claim 7, wherein the vacuum producing member is a piston.

14. The device of claim 7, wherein the vacuum producing member is a bellows.

15. The device of claim 7, wherein the first chamber is within a syringe barrel.

16. A device for differentiating type of blood vessel accessed by a cannula, for use in syringes and guidewire placement devices, comprising:
   (a) a first chamber in flow communication with the cannula;
   (b) a vacuum-producing member within the first chamber;
   (c) a pressure displaceable member, the pressure displaceable member being displaceable in response to venous and arterial pressure within the blood vessel accessed by the cannula;
   (d) a second chamber;
   (e) a resilient member within the second chamber opposing the displacement of the pressure displaceable member; and
   (d) patency means to allow guidewire insertion or fluid administration through the cannula.

17. The device of claim 16, wherein the patency means includes means for releasably connecting the first chamber with the cannula to allow reconnection of the cannula to other devices and to allow guidewire insertion and intravascular administration of fluids through the cannula.

18. The device of claim 16, wherein the patency means includes passageways to allow guidewire insertion through the cannula.

* * * * *